United States Patent [19]

Hinrichs et al.

[11] Patent Number: 5,395,324
[45] Date of Patent: Mar. 7, 1995

[54] APPARATUS FOR THE RELIABLE FILLING OF THE CONTAINER OF AN INFUSION PUMP

[75] Inventors: Jürgen Hinrichs; Karl-Heinz Otto, both of Kiel, Germany

[73] Assignee: Anschütz + Co., GmbH, Kiel, Germany

[21] Appl. No.: 157,164

[22] PCT Filed: Jun. 3, 1992

[86] PCT No.: PCT/DE92/00466
§ 371 Date: Jan. 13, 1994
§ 102(e) Date: Jan. 13, 1994

[87] PCT Pub. No.: WO92/21390
PCT Pub. Date: Dec. 10, 1992

[30] Foreign Application Priority Data
Jun. 7, 1991 [DE] Germany .................. 9107030 U

[51] Int. Cl.[6] .................... A61M 37/00; A61M 11/00
[52] U.S. Cl. .................... 604/86; 604/93; 604/132
[58] Field of Search .............. 604/86, 88, 93, 132, 604/133, 175, 201, 205, 244, 890.1, 891.1

[56] References Cited

U.S. PATENT DOCUMENTS

| | | | |
|---|---|---|---|
| 4,692,146 | 9/1987 | Hilger | 604/93 |
| 4,892,518 | 1/1990 | Cupp et al. | 604/93 |
| 4,955,861 | 9/1990 | Enegren et al. | 604/93 |
| 4,978,338 | 12/1990 | Melsky et al. | 604/86 |
| 5,167,638 | 12/1992 | Felix et al. | 604/244 |

OTHER PUBLICATIONS

PCT Application—Pub. No. WO89/10157, Nov. 2, 1989, Inventers: Enegren et al.
PCT Application—Pub. No. WO89/10149, Nov. 2, 1989, Inventers: Melsky et al.

*Primary Examiner*—John D. Yasko
*Assistant Examiner*—Frank Wilkens, III
*Attorney, Agent, or Firm*—Herbert W. Larson

[57] ABSTRACT

Apparatus for the reliable filling of at least two containers below the skin surface, particularly of an infusion pump, with two septa made from a soft material, so that easy perforation by needles is possible and further seals which are positioned after the septa, at least one space being in each case provided between the seals and the septa connected to the catheters or containers to be filled, in the case of different septa said spaces being at different distances from a needle stop, a corresponding number of needles with lateral openings for filling purposes are provided and the openings for different needles are at different distances (A, B) from the needle tip.

6 Claims, 1 Drawing Sheet

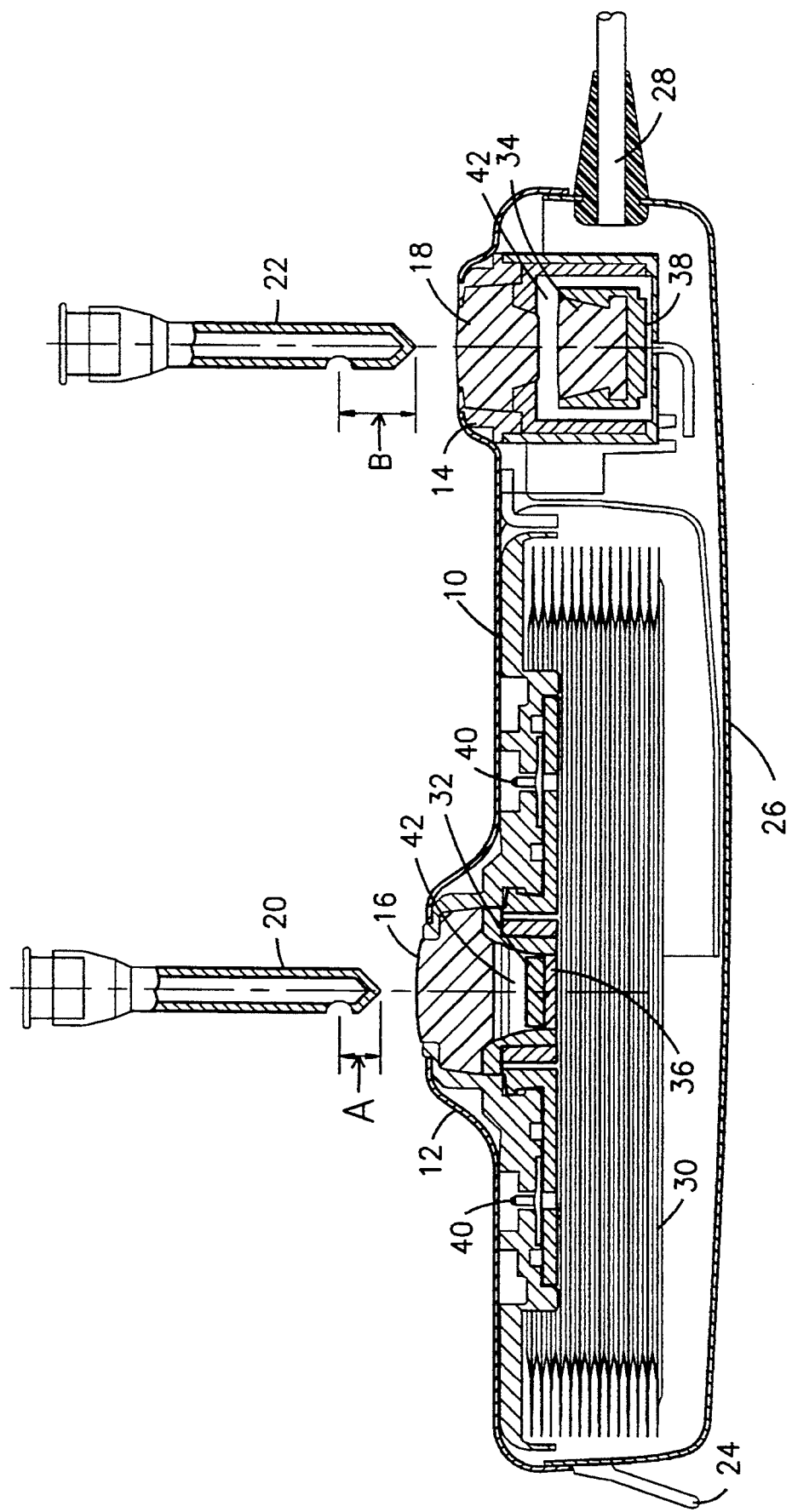

APPARATUS FOR THE RELIABLE FILLING OF THE CONTAINER OF AN INFUSION PUMP

BACKGROUND OF THE INVENTION

The invention relates to an apparatus for the reliable filling of at least two containers below the skin surface, particularly of an infusion pump with at least one septum.

Implantable infusion pumps are used for the continuous delivery of medicaments, e.g. morphines in a constant dosage over long periods of time. Compared with conventional injections they have the advantage that there is no longer any need to overdose to such an extent that despite the decomposition of the medicament up to the next administration time, there is no drop below a certain minimum dose and instead it is possible to achieve a uniform and significantly reduced supply of the medicament.

SUMMARY OF THE INVENTION

Increasingly more frequently the possibility is provided of administering with a syringe in a container of the infusion pump a so-called bolus dose, which then passes to the desired location via an already fitted catheter of the infusion pump. The aim of said bolus dose is to administer, under specific medical conditions, an increased medicament quantity for a short time and subsequently the infusion pump resumes its normal activity.

Up to now problems have been encountered on filling the containers in the body. At present it is not possible to completely reliable prevent a person introducing a new filling into the infusion pump from reaching the incorrect container, namely that for the bolus dose, so that the patient carrying the infusion pump receives his e.g. monthly dose as a bolus dose, which can in extreme cases be life-threatening.

The problem of the invention is to provide an apparatus for avoiding such problems and to ensure a reliable refilling.

According to the invention this is achieved in that two septa made from a soft material are provided and which can be easily perforated by needles and following which there are further seals or packings. In each case a space between the seals is linked with the catheters or containers to be filled. In the case of different septa said spaces are at different distances from the needle stop. A corresponding number of needles with lateral openings for filling purposes are provided, the openings for the different needles are constructed at different distances from the tip or point of the needles.

A preferred embodiment of the invention is described hereinafter together with its advantages and further features, by means of the subclaims, the specific technical description and the single drawing showing an infusion pump in sectional form and having two different needles for the refilling of the medicament container and for bolus dosing via the particular septa.

DESCRIPTION OF THE DRAWING

FIG. 1 is a side sectional elevational view of the device of this invention.

DETAILED DESCRIPTION OF THE INVENTION

The drawing shows the casing 10 with the two flattened and rounded shoulders 12, 14 projecting upwards from the casing and which serve to receive the septa 16, 18 and the needles 20, 22 to be used. It is possible to clearly see the two different distances A and B for the lateral openings of the needles 20, 22 with respect to the tip of the latter.

The fixing rings 24 on the casing bottom 26 are only shown from the side. They are positioned in such a way that it is possible to sew with a minimum thread length, so that the infusion pump cannot slip. From said infusion pump passes a catheter 28 to the location where the medicament is to be delivered, e.g. the vertebral column.

As a function of the desired delivery and the size of the infusion pump it will only be filled at long intervals, typically of one month. For this purpose use is made of the special needles 20, 22, which can pass in splinter-free manner through the silicone rubber septa 16, 18 provided in the cover 10. The opening of the said needles 20, 22 is not at the tip, but on the side at different distances from the tip.

The septa 16, 18 rest within the shoulders 12, 14, so that they can be felt from outside the skin. Confusion, e.g. resulting from the incorrect positioning of the infusion pump, in the case of the needles 20, 22 no longer leads to incorrect medication. If the incorrect septum is chosen, the seals alongside the septum seal the openings in the needle and no liquid can pass into the infusion pump.

A septum 16 for filling a medicament container from a spring bellows 30 and a further septum 18 for a bolus dose, i.e. an immediate supply, are juxtaposed on the casing cover, the septum for the bolus dose 18 being smaller and further towards the edge. As a result of the asymmetrical shape a distinguishing is possible by feeling from the outside in order to assist the person performing the injection.

As far as possible titanium is used for all parts and this is not only for strength reasons, but because the material is chemically very resistant, biocompatible and also very light.

Behind each septum is provided a plastic needle stop 38 at the lower end of each septum sleeve, which is also covered by a seal 32, 34, so that no "normal" needles with openings in the tip can accidentally fill the incorrect container.

The catheter 28 is fixed rotatably towards the side on the infusion pump casing, so that during implantation it is not fixed to a preferred body side. Besides the septa 16 there are two actuating elements 40 on the top of the infusion pump enabling the pump delivery rate to be adjusted.

We claim:

1. Apparatus for the reliable filling of at least two containers below the skin surface of an infusion pump comprising a first and second septa juxtaposed to each other, each having a top and bottom surface, the first and second septa made from a soft material for perforation by a needle, a first and second seal located below the first and second septa respectively, each seal having a top and bottom surface, the seal top surface spaced apart from the bottom surface of each first and second septum respectively, the spaced apart portion between the bottom surface of the first and second septa and the top surface of the first and second seal respectively adapted to receive a medicament from a needle, a first needle stop adjacent and below the bottom surface of the first seal and a second needle stop adjacent and below the bottom surface of the second seal, the first seal having a narrower depth than the second seal, a first needle for the first septum having a lateral filling opening spaced from the first needle tip a distance corresponding to the depth of the first seal, a second needle for the second septum having a lateral filling opening spaced from the second needle tip a distance corresponding to the depth of the second seal so that insertion of either the first or second needle into the wrong septum will result in no flow of medicament.

2. Apparatus according to claim 1, wherein the septa are made from silicone rubber.

3. Apparatus according to claim 1 wherein at least one of the septa is constructed on an inwardly directed end with a reduced diameter and rests on a relatively thick web.

4. Apparatus according to claim 1 wherein at least one of the septa is provided on its outwardly directed end with a channel which receives a casing cover or the wall of a septum sleeve.

5. Apparatus according to claim 4 wherein over an edge of an outwardly directed end of at least one of the septa there projects a bevelled part of the casing cover or the wall of a septum sleeve.

6. Apparatus according to claim 1 wherein at least one of the seals has at an end directed towards the needle stop a plate-like shoulder which projects over the diameter of the seal.

* * * * *